US011607347B2

(12) United States Patent
Park (10) Patent No.: US 11,607,347 B2
(45) Date of Patent: Mar. 21, 2023

(54) THERMOPLASTIC CAST (71) Applicant: OPENM INC., Daejeon (KR)

(72) Inventor: Jong Chil Park, Daejeon (KR)

(73) Assignee: OPENM INC., Daejeon (KR)

( * ) Notice: Subject to any disclaimer, the term of this patent is extended or adjusted under 35 U.S.C. 154(b) by 611 days.

(21) Appl. No.: 15/557,460

(22) PCT Filed: Aug. 3, 2016

(86) PCT No.: PCT/KR2016/008565
§ 371 (c)(1),
(2) Date: Sep. 11, 2017

(87) PCT Pub. No.: WO2017/023115
PCT Pub. Date: Feb. 9, 2017

(65) Prior Publication Data
US 2018/0055695 A1    Mar. 1, 2018

(30) Foreign Application Priority Data

Aug. 4, 2015  (KR) ........................ 10-2015-0110136
Aug. 2, 2016  (KR) ........................ 10-2016-0098526

(51) Int. Cl.
*A61F 13/04* (2006.01)
*A61F 5/05* (2006.01)
(Continued)

(52) U.S. Cl.
CPC ................ *A61F 13/04* (2013.01); *A61F 5/05* (2013.01); *A61L 15/07* (2013.01); *A61L 15/14* (2013.01)

(58) Field of Classification Search
CPC ........ A61F 13/04; A61F 13/041; A61F 13/02; A61F 13/022; A61F 13/0226;
(Continued)

(56) References Cited

U.S. PATENT DOCUMENTS 4,193,395 A * 3/1980 Gruber ................. A61F 5/0106
264/DIG. 30
6,673,029 B1 1/2004 Watson
(Continued)

FOREIGN PATENT DOCUMENTS

CN    104739558 A    7/2015
JP    H08-503150 A   4/1996
(Continued)

OTHER PUBLICATIONS

"Polyethylene", All About Plastic Moulding, Section LDPE Properties, http://www.plasticmoulding.ca/polymers/polyethylene.htm (Year: 2019).*
(Continued)

*Primary Examiner* — Kim M Lewis
(74) *Attorney, Agent, or Firm* — Maschoff Brennan (57) ABSTRACT

A thermoplastic cast according to an embodiment of the present invention includes a structure having a mesh form and a thermoplastic property, an outer cover provided on an outer surface of the structure, a buffer pad provided on an outer surface of the outer cover and having elasticity, and a finishing material provided on an outer surface of the buffer pad and configured to come into contact with a user's body. Melting points of the outer cover, the buffer pad, and the finishing material are higher than that of the structure. The finishing material has a porosity different from that of the buffer pad.

16 Claims, 7 Drawing Sheets

(51) Int. Cl.
*A61L 15/14* (2006.01)
*A61L 15/07* (2006.01)

(58) Field of Classification Search
CPC .... A61F 13/025; A61F 13/0253; A61F 13/10;
A61F 13/101; A61F 5/01; A61F 5/0102;
A61F 5/0104; A61F 5/0118; A61F 5/013;
A61F 5/058; A61F 5/05825; A61F
5/05841; A61F 5/05858; A61F 5/05866;
A61L 15/07; A61L 15/08; A61L 15/14
See application file for complete search history.

(56) References Cited

U.S. PATENT DOCUMENTS

| | | | | |
|---|---|---|---|---|
| 7,985,192 | B2* | 7/2011 | Sheehan | A61F 5/01 602/7 |
| 8,303,527 | B2* | 11/2012 | Joseph | A61F 13/046 602/8 |
| 10,632,007 | B2* | 4/2020 | Park | A61F 5/058 |
| 2002/0177797 | A1* | 11/2002 | Henderson | B29C 70/222 602/6 |
| 2005/0222529 | A1* | 10/2005 | Cuypers | A61F 13/04 602/20 |
| 2006/0084333 | A1* | 4/2006 | Watson | A61F 13/04 442/42 |
| 2008/0154164 | A1 | 6/2008 | Sheehan et al. | |
| 2014/0034058 | A1 | 2/2014 | Lang et al. | |
| 2014/0039366 | A1* | 2/2014 | Joseph | A61F 5/05825 602/7 |
| 2014/0147472 | A1* | 5/2014 | Elimelech | A61L 24/046 424/78.38 |
| 2016/0242949 | A1 | 8/2016 | Park et al. | |
| 2017/0042715 | A1 | 2/2017 | Park | |

FOREIGN PATENT DOCUMENTS

| | | | |
|---|---|---|---|
| JP | 3051373 U | 8/1998 | |
| KR | 10-2011-0047070 A | 5/2011 | |
| KR | 10-2012-0114104 A | 10/2012 | |
| KR | 20140070824 A | 6/2014 | |
| KR | 10-1414493 B1 | 7/2014 | |
| KR | 10-1425883 B1 | 8/2014 | |
| KR | 10-1538642 B1 | 7/2015 | |
| KR | 10-1538644 B1 | 7/2015 | |
| KR | 10-1538645 B1 | 7/2015 | |
| WO | 94/10946 A1 | 5/1994 | |
| WO | WO-2015046863 A1 * | 4/2015 | A61F 5/01 |

OTHER PUBLICATIONS

3M Hot Melt Pressure Sensitive Adhesive—Safety Data Sheet, 3M, May 11, 2018, Section 9: Physical and Chemical Properties, https://multimedia.3m.com/mws/mediawebserver?mwsId=SSSSSuUn_zu8I00xIY_ZMYt9Nv70k17zHvu9IxtD7SSSSSS—(Year: 2018).*

3M Thinsulate Insulation Type FX Stretch—Technical Data Sheet, 3M, Aug. 2016, http://multimedia.3m.com/mws/media/745357O/3m-thinsulate-insulation-type-fx-technical-data-sheet-pdf.pdf?fn=THN_TDS_Type-FX_06_keyline.pdf (Year: 2016).*

Enclose definition. Merriam Webster Online Dictionary, definition 1a. https://www.merriam-webster.com/dictionary/enclose (Year: 2020).*

Confine definition. Merriam Webster Online Dictionary. definition 1a. https://www.merriam-webster.com/dictionary/confine (Year: 2020).*

Mesh definition. The Free Dictionary, definition 1a. https://www.thefreedictionary.com/mesh (Year: 2020).*

Mesh definition, definition 1a, https://www.thefreedictionary.com/mesh (Year: 2021).*

Mearthane Products Corporation: Knowlegdge Center—Polyurethane Temperature Range, http://knowledgecenter.mearthane.com/polyurethanetemperaturerange (Year: 2021).*

Ministry of Supply: Glass Transition Temperature—The Secret to Wrinkle Resistant Fabrics, https://blog.ministryofsupply.com/blog/2019/2/27/yv3o4b7ffspsvy3rz5g8vp2kcr7cf1 (Year: 2021).*

Foam Tech—Open Cell Foam vs Closed Cell Foam, https://www.foamtechchina.com/open-cell-foam-vs-closed-cell-foam/ (Year: 2021).*

Epps, et al., Pore Size and Air Permeability of Four Nonwoven Fabrics, Internal Nonwovens Journal, https://journals.sagepub.com/doi/pdf/10.1177/1558925000OS-900215 (Year: 2021).*

Zhang, et al., Correlation between the acoustic and porous cell morphology of polyurethane foam, Elsevier Materials & Design, https://www.sciencedirect.com/science/article/pii/S0261306912002749 (Year: 2021).*

Chemical Book, Poly(Thylene TEREPHTHALATE,2010. https://www.chemicalbook.com/ChemicalProductProperty_EN_CB6493400.htm (Year: 2010).*

AU Examination Report in Application No. 2016303877 dated Apr. 24, 2020.

CN Office Action in Application No. 201680045632.7 dated Jun. 14, 2019.

CN Office Action in Application No. 201680045632.7 dated Sep. 27, 2020.

CN Search Report in Application No. 201680045632.7 dated Jun. 5, 2019.

CN Office Action in Application No. 201680045632.7 dated Jun. 1, 2020.

EP Search Report in Application No. 16833351.6 dated Oct. 29, 2019.

IN Office Action in Application No. 201817007293 dated May 26, 2020.

JP Notice of Reason for Rejection in Application No. 2017-547569 dated Aug. 16, 2018.

JP Notice of Reason for Rejection in Application No. 2019-017434 dated May 29, 2020.

ID Office Action in Application No. P00201801522 dated Feb. 6, 2020.

SG Search Report and Written Opinion in Application No. 11201800906V dated Feb. 21, 2019.

* cited by examiner

THERMOPLASTIC CAST

TECHNICAL FIELD

The present invention relates to a thermoplastic cast, and more particularly, to a thermoplastic cast formed of a thermoplastic material and capable of preventing movement of a damaged part (affected area) of a human being or an animal during a treatment process.

BACKGROUND ART

A cast, a splint a brace, a correction device, other medical correction devices, etc. for smooth treatment when a joint, an arm, or a leg is fractured or damaged are collectively referred to as a cast.

Generally, in order to fix a damaged joint, arm, or leg, a cast is put thereon using a bandage and plaster. However, the plaster is heavy and cannot be remolded once dried and deteriorates or is broken when exposed to moisture. Thus, it is difficult for a patient who wears a cast to bathe or shower. Furthermore, a part of the patient on which the cast is put is poorly ventilated.

Examples of a cast which is not easily damaged and has good ventilation include a water curable cast disclosed in U.S. Pat. No. 6,673,029, a water curable cast disclosed in Korean Patent Publication No. 10-1425883, and the like.

However, the disclosed water curable casts are low productivity since they should be prevented from coming into contact with water or moisture while being manufactured, are difficult to store since they should be air-tightly stored to protect them from moisture after being manufactured, and cannot be reused once they are hardened. Thus, water curable casts cannot be changed or reused even when change is necessary according to a patient's recovery state.

To solve these problems, Korean Patent Publication Nos. 10-1414493 and 10-1538642 disclose thermoplastic casts which have a core to have sufficient strength.

Korean Patent Publication Nos. 10-1538644 and 10-1538645 disclose a structure in which a soft outer cover is provided on an outer circumferential surface to serve as a stiffener and a change limiting element and prevent a patient from feeling uncomfortable even when a surface of a cast is in contact with the patient's skin.

However, such well-known casts may increase inconvenience of a patient since the casts have a hard surface or should be in contact with the patient's skin for a long time, and may cause pain to occur in a damaged area when an impact is applied thereto.

Figure 1:
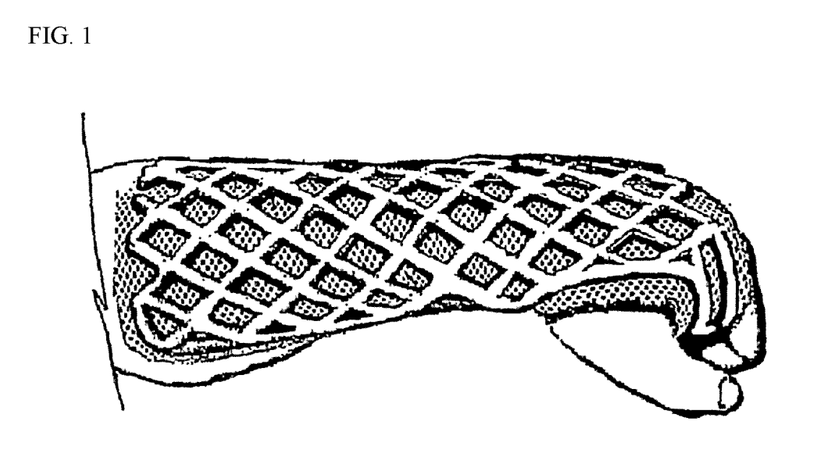
FIG. 1 is a diagram illustrating an installation example of a lower pad and a cast according to the related art.

Therefore, conventionally, a lower pad (or a skin protector) which is in a relatively fine mesh form is put around a damaged area before a cast is put on the damaged area, and then the diseased area is cured by fixing the cast on the lower pad, as illustrated in FIG. 1. In this case, the damaged area is poorly ventilated due to the lower pad, and the lower pad is wet for a long time, for example, when a patient showers and water is absorbed into the lower pad. Thus, the user would feel uncomfortable.

DISCLOSURE

Technical Problem

In order to solve the above-described problems of a conventional cast formed of a thermoplastic material and having a mesh form, the present invention is directed to a cast which includes a buffer pad formed of a foam and stacked on an interface between the cast and a user's skin to eliminate inconvenience to the user which may be caused when the user wears the cast, absorb an impact applied to a damaged area, have good ventilation, and be wearable and durable.

Technical Solution

One aspect of the present invention provides a thermoplastic cast having a structure in a mesh form, in which a plurality of lines for covering and fixing a user's body intersect each other in a diagonal direction, and a buffer pad formed of a foam is stacked on an interface between the structure and the user's skin.

In the thermoplastic cast, an outer cover formed of rubber may be attached to an outer circumferential surface of the structure and a mesh form core may be included in the structure.

The buffer pad may include two or more layers having different degrees of foaming.

In the buffer pad according to the present invention, the foam may include one or more types of resin selected from the group consisting of polyethylene, polypropylene, ethylene vinyl acetate, and polyurethane. The buffer pad may be bonded to the structure by insert injection molding without using an adhesive.

The buffer pad according to the present invention has a Shore C hardness of 45 or less.

Advantageous Effects

A cast having a mesh form structure according to the present invention includes a buffer formed of a foam and stacked on an interface between the cast and a user's skin to remove any inconvenience to the user caused when the user wears the cast, absorb an impact applied to a diseased area, and be wearable and durable.

BEST MODE OF THE INVENTION

A thermoplastic cast according to the present invention may be implemented on the basis of claim 1.

[Modes of the Invention]

Hereinafter, exemplary embodiments of the present invention will be described in detail with reference to the appended drawings, but the idea of the present invention is not limited thereto. Those of ordinary skill in the art who understand the idea of the present invention may easily suggest other regressive inventions or other embodiments falling within the scope of the present invention by adding, changing, or omitting other components within the same scope as the present invention, and it should be understood that the other regressive inventions or the other embodiments fall within the scope of the present invention.

In the drawings, the same reference numerals are allocated to components having the same functions falling within the same scope as the embodiments set forth herein.

Hereinafter, exemplary embodiments of the present invention will be described in detail with reference to the accompanying drawings.

Figure 2:
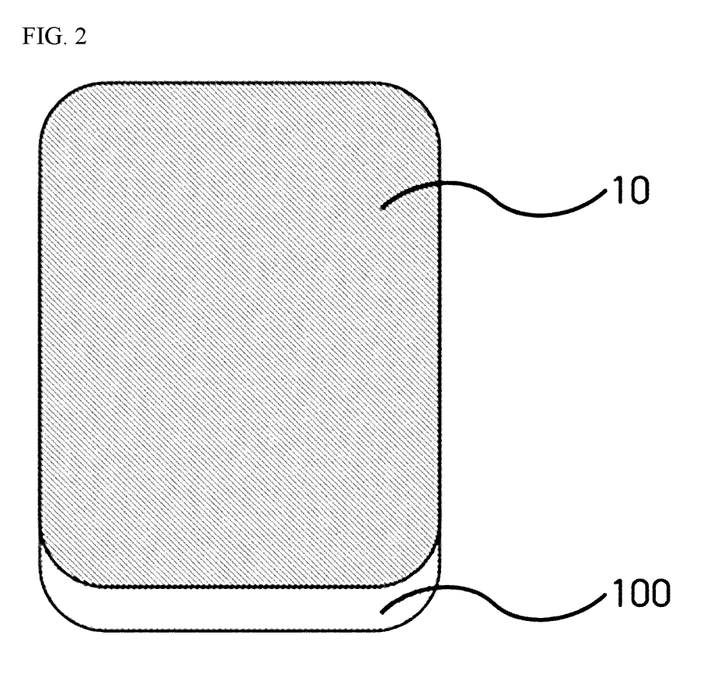
FIG. 2 is a cross-sectional view of a thermoplastic cast including a buffer pad stacked thereon according to an embodiment of the present invention.

The present invention relates to a composition of a thermoplastic cast for covering and fixing or correcting a patient's fractured part or the like. As illustrated in FIG. 2, a cast according to the present invention includes a structure 10 and a buffer pad 100 formed of a foam and stacked on a surface of the structure contacted to a user's skin.

The structure 10 has a mesh form in which openings each having a polygonal shape are uniformly formed. In this case, a cross section of a side of the structure 10 which is in the mesh form is molded in a rectangular shape, the height of which is greater than a width thereof to secure strength sufficient to resist an external force or impact. The structure 10 is formed of a polycaprolactone (PCL) composite with a PCL base.

Figure 3:
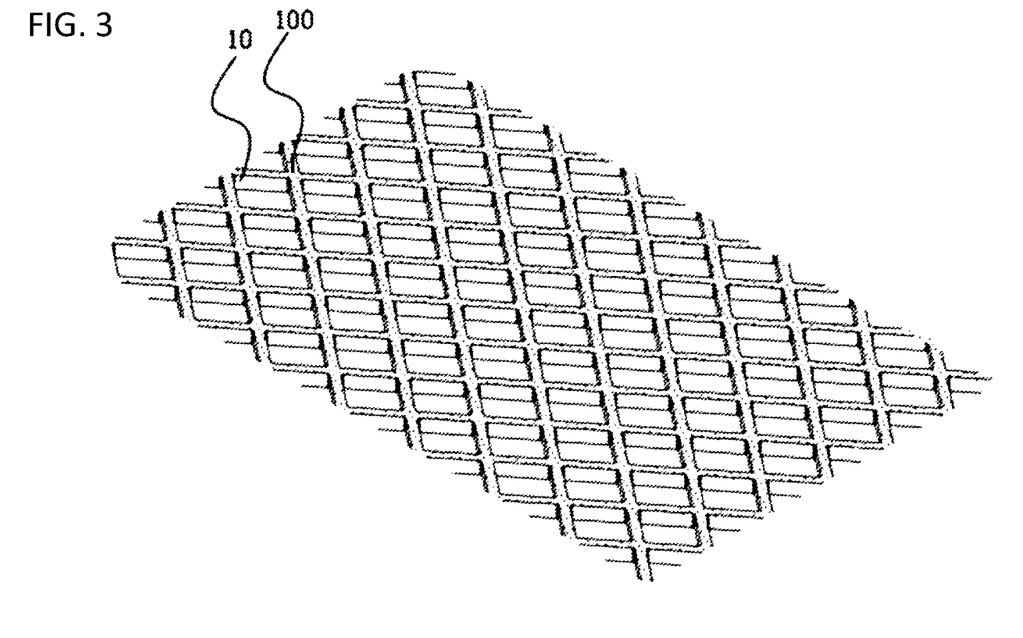
FIG. 3 is an outside view of a thermoplastic cast including a buffer pad thereon according to the present invention.

An overall shape of the cast including the structure 10 may be the same as or similar to those of the casts disclosed in Korean Patent Publication Nos. 10-1425883, 10-1414493, 10-1538642, 10-1538644, and 10-1538645 which were previously invented by the inventor of the present invention. As illustrated in FIG. 3, the buffer pad 100 is stacked on an overall surface of the structure 10 having a mesh form obtained by a plurality of lines being intersected and which is in contact with a user's skin.

PCL is used as a main ingredient of the PCL composite used to form the structure 10. The PCL employed in the present invention is a type of polyester produced through ring opening polymerization of caprolactone, is a crystalline polymer, and has a low melting point of 50 to 80° C.

Furthermore, the PCL employed in the present invention has a weight-average molecular weight of 20,000 to 80,000. When the average molecular weight of the PCL is less than 20,000, a mechanical physical property (impulse strength) of the PCL composite is low, and thus the PCL is not expected to serve as a structure. Thus, PCL with a high molecular weight is preferably used. However, when the weight-average molecular weight of the PCL is greater than 80,000, a modulus and flowability of the PCL composite are low and the PCL is not appropriate as a molding material.

A melting point of the PCL is in a range of about 50 to 80° C. under the above-described condition. Thus, the cast may be easily put on a damaged area.

However, when the structure 10 is formed of only the PCL, the physical properties thereof, e.g., tensile strength, are low, and thus a glass fiber or a carbon fiber may be added as a strength reinforcing material to the PCL to improve the physical properties.

Figure 4:
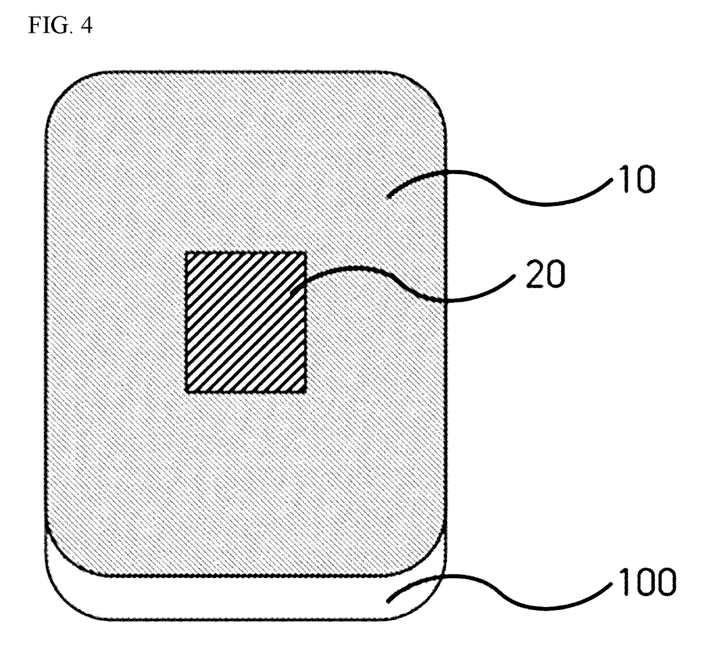
FIG. 4 is a cross-sectional view of a thermoplastic cast including a buffer pad stacked thereon according to another embodiment of the present invention.

In another embodiment, as illustrated in FIG. 4, a structure 10 including a core 20 therein and a buffer pad 100 formed of a foam and stacked on an interface between the structure 10 and a user's skin are provided.

Preferably, the core 20 is formed of a thermoplastic synthetic resin elastomer and has a melting point higher than that of the structure 10. In this case, a material of the core 20 having the higher melting point than that of the structure 10 may be an elastic material such as polyurethane, polyethylene, a soft PVC, a polypropylene copolymer, etc. In this case, each side of the structure 10 has a rectangular cross sectional shape, the height of which is greater than a width thereof. Thus, the structure 10 has strength sufficient to resist an external force or impact.

Figure 5:
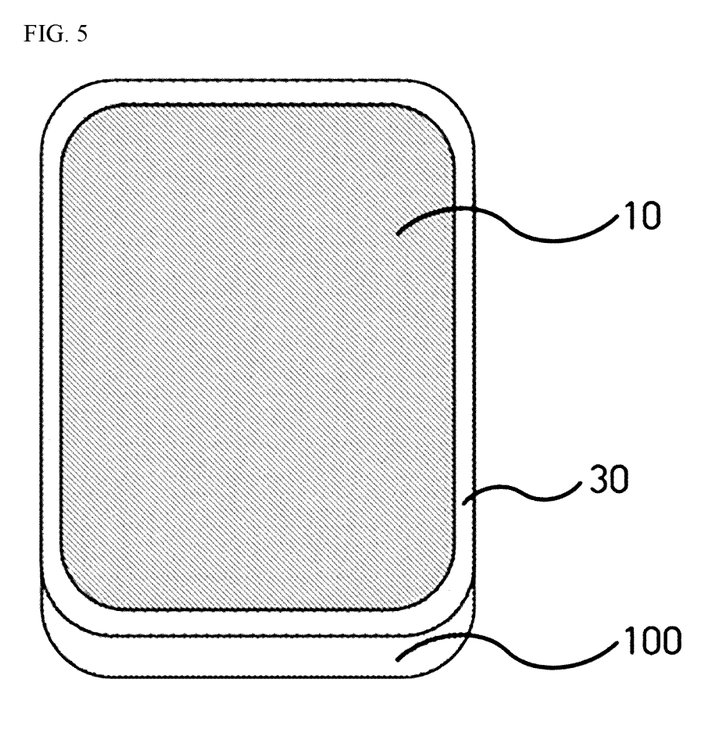
FIG. 5 is a cross-sectional view of a thermoplastic cast including a buffer pad stacked thereon according to additional embodiment of the present invention.

In an additional embodiment, as illustrated in FIG. 5, a structure 10 to which an outer cover 30 formed of rubber is attached, and a buffer pad 100 formed of a form and stacked on an interface between the structure 10 and a user's skin are provided.

In this case, the outer cover 30 covers the structure 10 to prevent the structure 10 from excessively extending when the structure 10 is melted such that the structure 10 may maintain a rectangular shape in a mesh form, may prevent a thickness of the structure 10 from being decreased when the structure 10 is elongated to prevent a decrease in the strength of the structure 10, and may serve as a buffer preventing a hard surface of the structure 10 from coming into direct contact with a patient's skin.

However, the outer cover 30 should exhibit both appropriate strength and elasticity, and is thus formed of a rubber material of a Shore D of 2 to 35. Thus, the outer cover 30 decreases a feeling of wearing the cast when the cast is in contact with the patient's skin and does not sufficiently absorb an external impact. Thus, the outer cover 30 exhibits a certain extent of cushioning function in comparison to a structure having no outer cover, but does not provide a sufficient cushioning effect.

Figure 7:
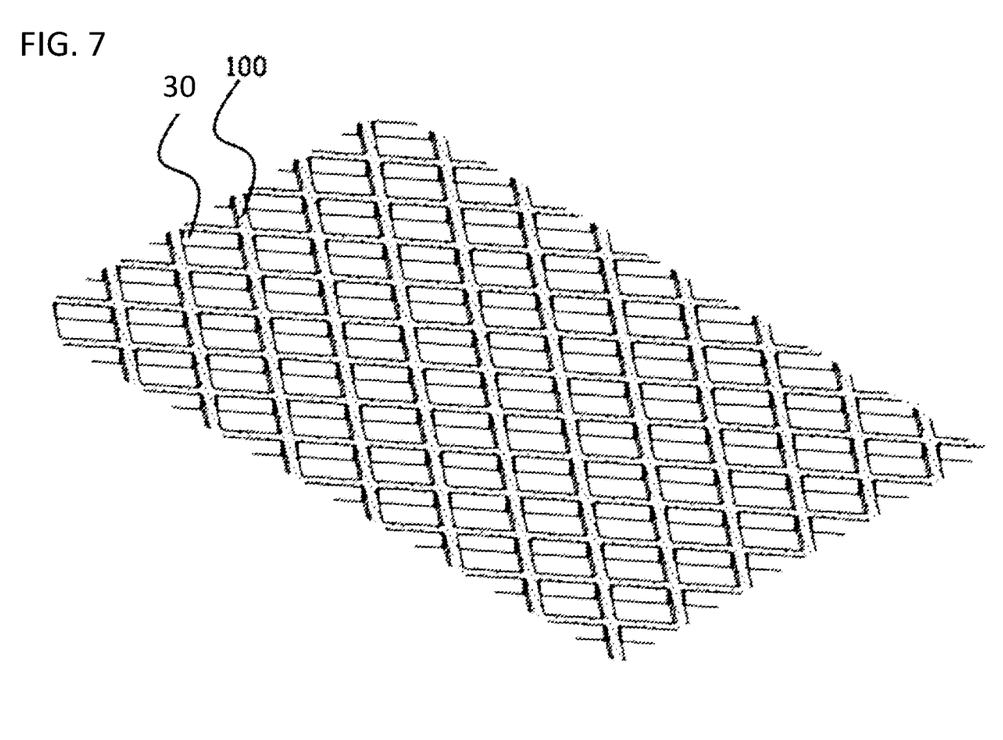
FIG. 7 is an outside view of a thermoplastic cast including a buffer pad thereon according to the present invention.

Thus, a desired effect of the present invention may be achieved when a buffer pad formed of a foam is stacked on an interface between the structure 10 including the outer cover 30 according to the present embodiment and a user's skin. As illustrated in FIG. 7, the buffer pad 100 is stacked on an overall surface of the outer cover 30 (with structure 10 therein as per FIG. 5) having a mesh form obtained by a plurality of lines being intersected and which is in contact with a user's skin.

In the present invention, the structure 10 should have high moldability when the structure 10 is heated to 70 to 80° C. to be put on a patient's damaged area, have strength sufficient to endure an external impact or force after the structure 10 is put on the damaged area, and have high flowability appropriate to manufacture the structure 10 through inject-molding.

The buffer pad stacked on the structure 10 should have high adhesive strength with respect to the structure 10 so as not to peel, be deformed, or broken due to an external force, moisture, heat, or the like.

Thus, the buffer pad according to the present invention is preferably formed of a foam. In this case, the foam is preferably manufactured by foaming one or more types of resin selected from the group consisting of polyethylene, polypropylene, ethylene vinyl acetate, and polyurethane.

In order to improve elasticity and flexibility, the resin may be mixed with one or more types of high elastic elastomers. The one or more types of high elastic elastomers include a styrene-based TPE such as EPR, EPDM, an ethylene-alpha olefin copolymer, SBS, SIS, or SEBS, a butadiene-based rubber material, a thermoplastic elastomer such as TPO, and a mixture thereof.

The mechanical strength, elasticity, and flexibility of the foam may vary according to a foam magnification. Thus, the foam magnification may be changed according to use of the cast. The foam magnification is preferably in a range of 5 to 40 times, and more preferably, in a range of 5 to 30 times.

When the foam magnification is low, the mechanical strength of the foam increases but the elasticity thereof decreases. When the foam magnification is excessively high or in the case of a non-cross-linked foam, a foamed cell may be broken at high temperatures, and thus a defective product may be produced. Thus, the foam magnification is preferably adjusted to be in the above-described range.

The buffer pad may be formed of two or more layers having different degrees of foaming.

When a cast having a mesh structure and a buffer pad having a high degree of foaming are fused to each other by fusion bonding, a foamed cell of the buffer pad is likely to explode during the fusion bonding, and thus an impact absorbing function of the buffer pad may not be smoothly performed and a fused state may be worsened. In contrast, a buffer pad having a low foaming degree has low impact absorbing capability and decreases a feeling of wearing a cast. Thus, explosion of the foamed cell of the buffer pad may be prevented and the impact absorbing capability may be improved when a pad having a low foaming degree and a pad having a high foaming degree are stacked together to form a sheet with two or more layers, a part having a low foaming degree is used as a fusing part, and a part having a high foaming degree is used as a part in contact with a user's skin.

Alternatively, a foam formed of a material having a low melting point, e.g., EVA, may be used as the part in contact with the user's skin and a foam formed of a material having a relatively high melting point, e.g., LDPE, may be used as a fusing part.

A process of foaming a buffer pad according to the present invention may be a cross-linking-foaming process or a non-cross-linking foaming process.

Examples of the cross-linking-foaming process include a chemical cross-linking-foaming process and an electron beam cross-linking-foaming process. In the chemical cross-linking-foaming process, a radical is formed at a high temperature, a sheet is molded by mixing a resin with a cross-linking agent which causes a cross-linking reaction to occur and a foam which decomposes and generates a gas at a high temperature, and then a resultant structure is extruded at a low temperature at which the cross-linking reaction and the foam decomposition reaction do not occur, and the foaming is generated through the cross-linking reaction by passing the molded sheet through an inside of a high-temperature horizontal tunnel.

In the electron beam cross-linking-foaming process, a non-foamed sheet is manufactured by mixing and extruding a foam and resin together without using a cross-linking agent, an electron beam is emitted toward this sheet to cause a cross-linking reaction to occur, and foaming is generated by passing the sheet through an inside of a high-temperature horizontal or vertical tunnel.

Examples of the non-cross-linking-foaming process include a method of using a chemical foam and a method of using a gas type foam. Here, foaming is generated by a primary extruding process without using a cross-linking reaction.

In this case, since the viscosity and elasticity of a cross-linked resin remarkably increase in a melted state, the cross-linked resin has smaller and more uniform bubbles than those of a non-cross-linked foamed sheet. Thus the foam has high elasticity and restoring force and feels soft. When the foam is not cross-linked, a thin bubble wall is quickly melted at a high temperature, and thus a cell is broken. Thus, non-cross-linking foaming is not appropriate for a buffer pad bonding process performed by an insert injection-molding process according to the present invention. Thus, a buffer pad is preferably manufactured by the cross-linking-foaming process or the electron beam cross-linking-foaming process.

A buffer pad and a structure according to the present invention are bonded to each other by insert injection-molding.

Examples of a method of bonding the buffer pad and the structure include a bonding method using an adhesive and a heat bonding method performed at a high temperature.

In the bonding method using an adhesive, a structure and a buffer pad are bonded to each other by applying the adhesive to a surface of the structure or an outer cover covering the structure, a surface of the buffer pad, or both of them, putting them together, and applying pressure thereto. Thus, bonding may be performed at a low temperature. However, this method is not preferable since it is complicated, a working place may be polluted due to the use of a liquid adhesive, and a harmful substance may remain in a completed cast.

In the heat bonding method, a surface of a structure or an outer cover to be bonded and a surface of a buffer pad are bonded to each other by heating them to a melting point or more at which the structure, the outer cover, and the buffer pad are melted, putting them together, and applying pressure thereto. This method is simpler than a high-temperature process or a process using an adhesive and is eco-friendly.

However, process efficiency of the heat bonding method is low, since a structure is molded by insert injection-molding or a structure covered with an outer cover is molded and then a process of bonding the structure with a buffer pad is additionally performed.

Thus, in the present invention, a bonding process is performed by bonding a buffer pad during an insert injection-molding process without performing an additional process.

That is, a sheet form buffer pad is cut in a shape of a structure and is then inserted into a core of a moving plate of a mold for molding the structure or an outer cover thereof.

In the case of a structure including an outer cover, a primarily molded structure is inserted into a mold and a rubber material for forming the outer cover is insert-molded such that a resin melted at a high temperature may be bonded to a buffer pad by heating as soon as the resin flows into the mold to form the outer cover. Thus, a cast in which the structure is covered with the outer cover and the buffer pad is bonded to a surface of the outer cover may be manufactured with one process.

In the case of a structure including no outer cover, a primarily molded structure is molded by injecting the structure into a mold, and a buffer pad which is cut in a shape of the structure is inserted into a core of a moving plate of the mold such that the structure may be bonded to the buffer pad by heating as soon as the structure is molded. Thus, a cast to which the buffer pad is bonded may be manufactured with one process.

It was determined that the buffer pad bonded to the cast should preferably have a density of 0.03 to 0.1 $g/cm^3$ and a Shore C hardness of 45 or less in the present invention.

When the density of the buffer pad is extremely high and beyond the above-described range, the buffer pad is extremely hard and greatly decreases the feeling of wearing the cast. When the density of the buffer pad is extremely low, the durability thereof decreases, and thus the buffer pad is likely to be broken or peeled. Therefore, the buffer pad is preferably manufactured to satisfy the above-described range.

When the Shore C hardness is extremely high and beyond the range, the buffer pad does not have sufficient elasticity and greatly decreases the feeling of wearing the cast. When the Shore C hardness is extremely low, the durability of the buffer pad decreases, and thus the buffer pad is likely to be broken. Therefore, the buffer pad is preferably manufactured to satisfy the above-described range.

In the present invention, the buffer pad and the structure are bonded with a sufficient adhesive strength. Thus, when the buffer pad is manufactured to have splitting resistance of 250 N/100 mm or more according to ASTM D903, the buffer pad is prevented from being peeled from the structure, and thus exhibits high adhesive strength. When the splitting resistance is not sufficient, the buffer pad partially peels or is damaged when a cast is pushed against the floor. Thus, it was determined that the appropriate splitting resistance is 250 N/100 mm or more.

The present invention will now be described in greater detail on the basis of examples below.

Example 1

An LDPE crosslinked foamed sheet manufactured by Yongbo Chemical Co., Ltd. and having a foam magnification of ten times and a thickness of 1 mm was cut in a mesh form, such as a mold cavity, and inserted into an injection mold cavity, and a structure manufactured by primarily inject-molding PCL reinforced with a glass fiber in a mesh form was placed in front of the foamed sheet inside a mold.

Then a TPE resin used as a material of an outer cover was insert injection-molded at 160 to 170° C. to manufacture a cast including a structure covered with the material of the outer cover and having the foamed sheet stacked as a buffer pad on a surface thereof.

Examples 2 to 9

As shown in Table 1 below, casts were manufactured in the same way as that in Example 1 but using foamed sheets having different foam magnifications, thicknesses, and materials.

Example 10

An LDPE crosslinked foamed sheet manufactured by Yongbo Chemical Co., Ltd. and having a foam magnification of ten times and a thickness of 1 mm was cut in a mesh form, such as a mold cavity, and inserted into an injection mold cavity.

A PCL composite reinforced with a glass fiber and used as a structure was insert injection-molded at 150° C. to manufacture a cast in a mesh form in which a foamed sheet is stacked as a buffer pad on a surface of the structure.

Examples 11 to 18

As shown in Table 1 below, casts were manufactured in the same way as that in Example 10 but using foamed sheets having different foam magnifications, thicknesses, and materials.

Comparative Example

A conventional cast in which an outer cover was insert injection molded by mounting only a structure in a mold without a buffer pad was manufactured.

TABLE 1

|  | Outer cover | Foamed resin | Foam magnification (times) | Foam thickness (mm) | Foam density (g/cm$^3$) | Foam hardness Shore C |
|---|---|---|---|---|---|---|
| Example 1 | Present | LDPE | 10 | 1 | 0.092 | 45 |
| Example 2 |  |  | 20 | 3 | 0.046 | 37 |
| Example 3 |  |  | 30 | 3 | 0.031 | 32 |
| Example 4 |  | LDPE/EVA | 10 | 1 | 0.093 | 41 |
| Example 5 |  |  | 20 | 3 | 0.046 | 32 |
| Example 6 |  |  | 30 | 3 | 0.032 | 29 |
| Example 7 |  | PP | 10 | 1 | 0.091 | 62 |
| Example 8 |  |  | 20 | 3 | 0.045 | 50 |
| Example 9 |  |  | 30 | 3 | 0.031 | 38 |
| Example 10 | Absent | LDPE | 10 | 1 | 0.092 | 45 |
| Example 11 |  |  | 20 | 3 | 0.046 | 37 |
| Example 12 |  |  | 30 | 3 | 0.031 | 32 |
| Example 13 |  | LDPE/EVA | 10 | 1 | 0.093 | 41 |
| Example 14 |  |  | 20 | 3 | 0.046 | 32 |
| Example 15 |  |  | 30 | 3 | 0.032 | 29 |
| Example 16 |  | PP | 10 | 1 | 0.091 | 62 |
| Example 17 |  |  | 20 | 3 | 0.045 | 50 |
| Example 18 |  |  | 30 | 3 | 0.031 | 38 |
| Comparative Example | Present | — | — | — | — | — |

\* LDPE: 3 MI/0.921 den., EVA: 15% VA, 1.8 MI, PP: PP Homopolymer, 3 MI
\* LDPE/EVA: LDPA 70 weight %, EVA 30 weight %

Characteristics of Buffer Sheet

In order to evaluate characteristics of the buffer sheet according to the foam magnification, a density, tensile strength, an elongation rate, tearing strength, a dimensional change by heat, hardness, and an appearance of an LDPE buffer sheet were evaluated while changing the foam magnification.

In the appearance evaluation, when the buffer sheet was viewed with the naked eye, "⊚" was marked when the buffer sheet had a good surface state and no defects, "○" was marked when there were no problems in using the buffer sheet despite some defects, "Δ" was marked when a foamed cell was partially deformed, and "x" was marked when a large part of a foamed cell exploded.

A result of evaluating the characteristics of the buffer sheet is shown in Table 2 below.

TABLE 2

|  |  | 5 times | 10 times | 15 times | 20 times | 25 times | 30 times | 40 times |
|---|---|---|---|---|---|---|---|---|
| Density (g/cm³) | | 0.018 | 0.092 | 0.067 | 0.046 | 0.04 | 0.031 | 0.023 |
| Tensile strength (kgf/cm²) | L | 19.5 | 14.2 | 12.0 | 8.3 | 6.3 | 5.3 | 4.2 |
|  | W | 12 | 7.4 | 6.3 | 4.2 | 3.3 | 2.9 | 2.1 |
| Elongation rate (%) | L | 464 | 308 | 295 | 202 | 150 | 130 | 113 |
|  | W | 294 | 243 | 239 | 174 | 125 | 112 | 103 |
| Tearing strength (kgf/cm) | L | 8.2 | 6.8 | 5.7 | 2.1 | 1.7 | 1.5 | 1.3 |
|  | W | 9.7 | 7.9 | 6.7 | 3.8 | 3.2 | 2.9 | 2.2 |
| Dimensional change by heat (80° C. × 1 h) | L | −1.1 | −1.3 | −1.5 | −2.3 | −2.5 | −3.3 | −3.6 |
|  | W | +0.3 | +0.3 | +0.3 | +0.6 | +0.7 | +0.7 | +0.9 |
| Hardness (Shore C) | | 60 | 45 | 41 | 37 | 34 | 32 | 27 |
| Appearance | | ⊚ | ⊚ | ⊚ | ⊚ | ○ | ○-Δ | X |

The result of evaluating the characteristics of the buffer sheet revealed that the buffer sheet having a good appearance and satisfying a Shore C hardness of 27 to 70 was achieved when the foam magnification was 5 to 30 times.

Furthermore, in order to evaluate characteristics of the buffer sheet while changing a type of resin thereof, a density, tensile strength, an elongation rate, tearing strength, a dimensional change by heat, hardness, and an appearance of each of an LDPE buffer sheet, an LDPE/EVA buffer sheet, and a PP buffer sheet were evaluated when the foam magnification was 20 times.

A result of evaluating the characteristics of the buffer sheet is shown in Table 3 below.

TABLE 3

|  |  | LDPE | LDPE/EVA | PP |
|---|---|---|---|---|
| Density (g/cm³) | | 0.046 | 0.042 | 0.045 |
| Tensile strength (kgf/cm²) | L | 8.3 | 7.7 | 11.3 |
|  | W | 4.2 | 3.9 | 6.3 |
| Elongation rate (%) | L | 202 | 224 | 295 |
|  | W | 174 | 165 | 239 |
| Tearing strength (kgf/cm) | L | 2.1 | 2.0 | 4.2 |
|  | W | 3.8 | 3.6 | 5.8 |
| Dimensional change by heat (80° C. × 1 h) | L | −2.3 | −1.3 | −3.6 |
|  | W | +0.6 | +0.3 | +0.5 |
| Hardness (Shore C) | | 37 | 29 | 58 |
| Appearance | | ⊚ | ○ | ⊚ |

Organic Function Test (the Feeling of Wearing)

An organic function test was conducted by putting the casts manufactured according to Examples 1 to 18 and the conventional cast according to Comparative Example which did not include a buffer pad on ten general men's arms and ten general women's arms to evaluate cushioning performance and a feeling of wearing the cast when the men and women wore the casts.

When three points were given with respect to the feeling of wearing the conventional cast which did not include a buffer pad and ten points were given with respect to the feeling of not wearing the cast, scores ranging from 1 to 10 points were given with respect to the feelings of wearing each of the casts according to Examples 1 to 18 in a real-life environment and an average of the scores was calculated.

TABLE 4

|  | Average score of the feelings of wearing the cast |
|---|---|
| Example 1 | 6.2 |
| Example 2 | 7.0 |
| Example 3 | 8.0 |
| Example 4 | 7.0 |
| Example 5 | 8.2 |
| Example 6 | 9.2 |
| Example 7 | 3.4 |
| Example 8 | 5.2 |
| Example 9 | 6.6 |
| Example 10 | 6.0 |
| Example 11 | 6.8 |
| Example 12 | 8.0 |
| Example 13 | 6.8 |
| Example 14 | 8.0 |
| Example 15 | 8.9 |
| Example 16 | 3.3 |
| Example 17 | 5.2 |
| Example 18 | 6.5 |
| Comparative Example | 3.0 |

A result of the organic function test revealed that the feelings of wearing the casts including the buffer pads according to Examples 1 to 18 were better than the feeling of wearing the conventional cast which included only the outer cover and did not include a buffer pad. However, a relatively lower score was given with respect to the feeling of wearing the cast in the case of an extremely thin PP buffer sheet having a foam thickness of 1 mm and a foam magnification of ten times. Thus, a foam thickness and a foam magnification should be adjusted according to a material of a buffer pad. In this case, the Shore C hardness was greater than 45, and thus the feeling of wearing the cast decreased to a large extent.

In the case of a PP buffer sheet having a foam magnification of 20 times, the Shore C hardness was greater than 45 and the average of the scores given with respect to the feeling of wearing the cast was 5.2, which was lower than those of the other examples. Thus, it was determined that satisfying a condition of the Shore C hardness being 45 or less is a major factor for improving a feeling of wearing a cast according to the present invention.

The reason why the application of the buffer pad according to the present invention was found to improve the feeling of wearing the cast is that the buffer pad relieved a hard and unnatural feeling when a surface of the cast was in direct contact with a user's skin.

Figure 6:
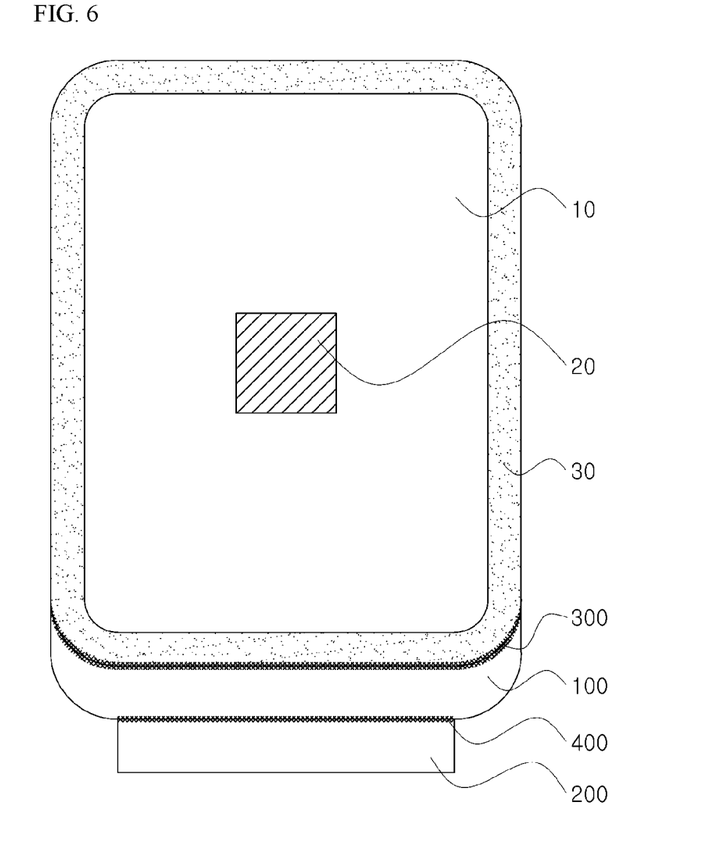
FIG. 6 is a cross-sectional view of a thermoplastic cast including a finishing material stacked thereon according to another embodiment of the present invention.

As illustrated in FIG. 6, a thermoplastic cast according to an embodiment of the present invention includes a structure 10 having a mesh form as described above and a thermoplastic property, an outer cover 30 provided on an outer surface of the structure 10, and a buffer pad 100 provided on an outer surface of the outer cover 30 and having elasticity. The thermoplastic cast may further include a finishing material 200 provided on an outer surface of the buffer pad 100 to be in contact with a user's body.

For example, the finishing material 200 may improve a feeling of wearing the cast when the cast is in contact with the user's body.

For example, melting points of the outer cover 30, the buffer pad 100, and the finishing material 200 may be higher than that of the structure 10.

Thus, only the structure 10 may be melted and the outer cover 30, the buffer pad 100, and the finishing material 200 may not be melted when heated to a certain temperature.

For example, the melting point of the buffer pad 100 may be higher than that of the outer cover 30.

For example, the finishing material 200 may have a porosity different from that of the buffer pad 100.

Furthermore, the finishing material 200 may have a friction coefficient different from that of the buffer pad 100.

For example, when the porosity of the finishing material 200 is greater than that of the buffer pad 100, the finishing material 200 may absorb sweat or moisture well.

In contrast, when the porosity of the finishing material 200 is less than that of the buffer pad 100, an area of the finishing material 200 which is in contact with the user's body is large, and thus the user will feel comfortable and a larger amount of heat may be transferred from the user's body to the finishing material 200.

Accordingly, one of a plurality of finishing materials having different physical properties may be selected as the finishing material 200 according to the season or an age or taste of the user and arranged on the outer surface of the buffer pad 100.

For example, the finishing material 200 may be a cloth, a fabric, a felt, a synthetic fiber, a natural fiber, a rubber, a synthetic resin, or the like.

However, the finishing material 200 is not limited thereto, and it should be obvious to those of ordinary skill in the art that various types of material may be selected as long as a comfortable feeling is given when the material is in contact with a user's body.

Similarly, the buffer pad 100 is not limited to the foam and may be a cloth, a fabric, a felt, a synthetic fiber, a natural fiber, a rubber, a synthetic resin, or the like.

The thermoplastic cast according to an embodiment of the present invention may further include a first layer 300 formed between the buffer pad 100 and the outer cover 30 and having a porosity different from those of the buffer pad 100 and the outer cover 30.

For example, the porosity of the first layer 300 may be less than that of the buffer pad 100. Thus, for example, a durability of the buffer pad 100 may be strengthened such that the buffer pad 110 may be prevented from being separated from the outer cover 30.

The first layer 300 may connect the outer cover 30 and the buffer pad 100.

The outer cover 30 may be connected to one surface of the first layer 300 and the buffer pad 100 may be connected to another surface of the first layer 300.

The first layer 300 may strengthen the durability of the buffer pad 100 and fix the buffer pad 100 at a predetermined location on the outer cover 30.

For example, a melting point of the first layer 300 may be higher than that of the structure 10.

For example, the first layer 300 may be formed of a material serving as an adhesive.

For example, the first layer 300 may be understood to be a region which is formed when the outer cover 30 is melted and located in an opening of the buffer pad 100 and in which the outer cover 30 and the buffer pad 100 coexist.

Alternatively, the first layer 300 may be understood to be a region which is formed when the buffer pad 100 is melted and located in an opening of the outer cover 30 and in which the outer cover 30 and the buffer pad 100 coexist.

The thermoplastic cast according to an embodiment of the present invention may further include a second layer 400 formed between the buffer pad 100 and the finishing material 200 and having a porosity different from those of the buffer pad 100 and the finishing material 200.

For example, the porosity of the second layer 400 may be less than those of the buffer pad 100 and the finishing material 200.

Thus, for example, the durability of the finishing material 200 may be strengthened such that the finishing material 200 may be prevented from being separated from the buffer pad 100.

The second layer 400 may connect the finishing material 200 and the buffer pad 100.

The buffer pad 100 may be connected to one surface of the second layer 400 and the finishing material 200 may be connected to another surface of the second layer 400.

The second layer 400 may strengthen the durability of the finishing material 200 and fix the finishing material 200 to a predetermined location on the buffer pad 100.

For example, a melting point of the second layer 400 may be higher than that of the structure 10.

For example, the second layer 400 may be formed of a material serving as an adhesive.

For example, the second layer 400 may be understood to be a region which is formed when the buffer pad 100 is melted and located in an opening of the finishing material 200 and in which the finishing material 200 and the buffer pad 100 coexist.

Alternatively, the second layer 400 may be understood to be a region which is formed when the finishing material 200 is melted and located in an opening of the buffer pad 100 and in which the finishing material 200 and the buffer pad 100 coexist.

For example, the first layer 300 may have a porosity different from that of the second layer 400.

For example, the porosity of the first layer 300 may be greater than that of the second layer 400.

Therefore, the first layer 300 may more firmly fix the buffer pad 100 onto the outer cover 30, and the second layer 400 may absorb sweat and moisture flowing into the opening of the finishing material 200.

While the structure and features of the present invention have been described above with respect to embodiments of the present invention, the present invention is not limited thereto, and it should be obvious to those of ordinary skill in the art that various changes or modifications may be made in the present invention without departing from the idea and scope of the invention. Accordingly, it should be understood that such changes or modifications fall within the scope of the invention as defined by the appended claims.

The invention claimed is:

1. A thermoplastic cast comprising:
   a structure of a mesh form in which uniformly arranged openings each having a polygonal shape are formed by a plurality of lines being intersected, each line having a body with a cross-sectional area with at least one external surface, the structure having a thermoplastic property such that the structure becomes flexible when heated;
   an outer cover which encloses the structure by covering each external surface of each line of the structure to form a core and shell cross-section with the core being one line portion and the shell being one outer cover portion such that the outer cover has a mesh form in which uniformly arranged outer cover openings are formed coextensive with the uniformly arranged openings of the mesh form of the structure, such that the outer cover is configured to confine each external surface of each line of the structure when the structure becomes flexible; and
   a buffer pad provided on an outer surface of the outer cover, the buffer pad being a foam and having elasticity;
   wherein the buffer pad has a body in a mesh form in which uniformly arranged buffer pad openings are formed into the body, wherein the buffer pad openings align with the outer cover openings,
   wherein the buffer pad is adhered to the outer cover with the outer cover between the buffer pad and the structure such that the buffer pad is deformed together with the structure when the heated structure is deformed to fit a fractured part of a patient's body.

2. The thermoplastic cast of claim 1, wherein each line has the cross-sectional area with a height and width.

3. The thermoplastic cast of claim 2, wherein each line has the height greater than the width.

4. The thermoplastic cast of claim 2, wherein each line has a core and shell cross-section, wherein the core includes a material having a higher melting temperature than a melting temperature of the shell.

5. The thermoplastic cast of claim 1, wherein the outer cover is formed of a rubber material.

6. The thermoplastic cast of claim 5, wherein the structure is polycaprolactone.

7. The thermoplastic cast of claim 6, wherein the polycaprolactone has a molecular weight of 20,000 to 80,000 Da.

8. The thermoplastic cast of claim 6, wherein the buffer pad is the foam having a density of about 0.03 to about 0.1 $g/cm^3$ and a Shore C hardness of about 45 or less.

9. The thermoplastic cast of claim 8, wherein the foam is selected from polyethylene, polypropylene, ethylene vinyl acetate, and polyurethane.

10. The thermoplastic cast of claim 9, wherein the foam includes an elastomer mixed therein.

11. The thermoplastic cast of claim 6, further comprising a finishing layer on a surface of the buffer pad, wherein the buffer pad is between the finishing layer and the outer cover.

12. The thermoplastic cast of claim 11, wherein the structure has a lower melting temperature than the outer cover, buffer pad, and finishing layer.

13. The thermoplastic cast of claim 11, wherein the finishing layer has a porosity higher than a porosity of the buffer pad.

14. The thermoplastic cast of claim 11, wherein the finishing layer has a porosity lower than a porosity of the buffer pad.

15. The thermoplastic cast of claim 1, wherein the body of the line includes a top external surface, bottom external surface, and two side external surfaces, wherein each of the top external surface, bottom external surface, and two side external surfaces has the outer cover thereon.

16. The thermoplastic cast of claim 1, wherein each external surface of the body has the outer cover thereon.

* * * * *